United States Patent [19]
Oyama et al.

[11] Patent Number: 5,205,920
[45] Date of Patent: Apr. 27, 1993

[54] ENZYME SENSOR AND METHOD OF MANUFACTURING THE SAME

[76] Inventors: Noboru Oyama, 5-24, Shinmachi 3-chome, Fuchu-shi, Tokyo; Takeshi Shimomura; Shuichiro Yamaguchi, both of c/o Terumo Kabushiki Kaisha : 1500, Inokuchi, Nakai-cho, Ashigarakami-gun, Kanagawa-ken, all of Japan

[21] Appl. No.: 487,372

[22] Filed: Mar. 2, 1990

[30] Foreign Application Priority Data

Mar. 3, 1989 [JP] Japan ................................. 1-51291
Mar. 28, 1989 [JP] Japan ................................. 1-76218

[51] Int. Cl.$^5$ ............................................. G01N 27/26
[52] U.S. Cl. ................................ 204/403; 204/412; 204/153.12
[58] Field of Search ................... 204/403, 412, 153.12

[56] References Cited

U.S. PATENT DOCUMENTS

| | | | |
|---|---|---|---|
| 4,711,245 | 12/1989 | Higgins et al. | 204/403 |
| 4,830,959 | 5/1989 | McNeil et al. | 204/403 |
| 4,836,904 | 6/1989 | Armstrong et al. | 204/403 |
| 4,897,173 | 1/1990 | Nankai et al. | 204/403 |
| 4,927,516 | 5/1990 | Yamaguchi et al. | 204/403 |

*Primary Examiner*—John Niebling
*Assistant Examiner*—Bruce F. Bell
*Attorney, Agent, or Firm*—Burns, Doane, Swecker & Mathis

[57] ABSTRACT

An enzyme sensor is disclosed, which has a two-layer fixed film structure consisting of a reduction function layer including an electron movement medium and di-valent iron ions and an enzyme-fixed layer covering said reduction function layer, and in which hydrogen peroxide generated through decomposition of glucose or the like in the enzyme-fixed layer is reduced by electron movement medium and di-valent iron ions in the reduction function layer.

Thus, the construction of enzyme sensor is simplified, measurement is extremely facilitated, and the measurement time is reduced.

As a different principle of enzyme sensor, an electrically conductive substrate of conductive carbon or the like is covered with an oxygen-reducing catalytic function layer and enzyme layer.

Thus, there is no problem of contamination of enzyme sensor, and it is possible to readily manufacture and miniaturize enzyme sensors.

4 Claims, 7 Drawing Sheets

100 mg/dl
— WITH GLUCOSE
---- WITHOUT GLUCOSE

ELECTRODE POTENTIAL VS. SSCE

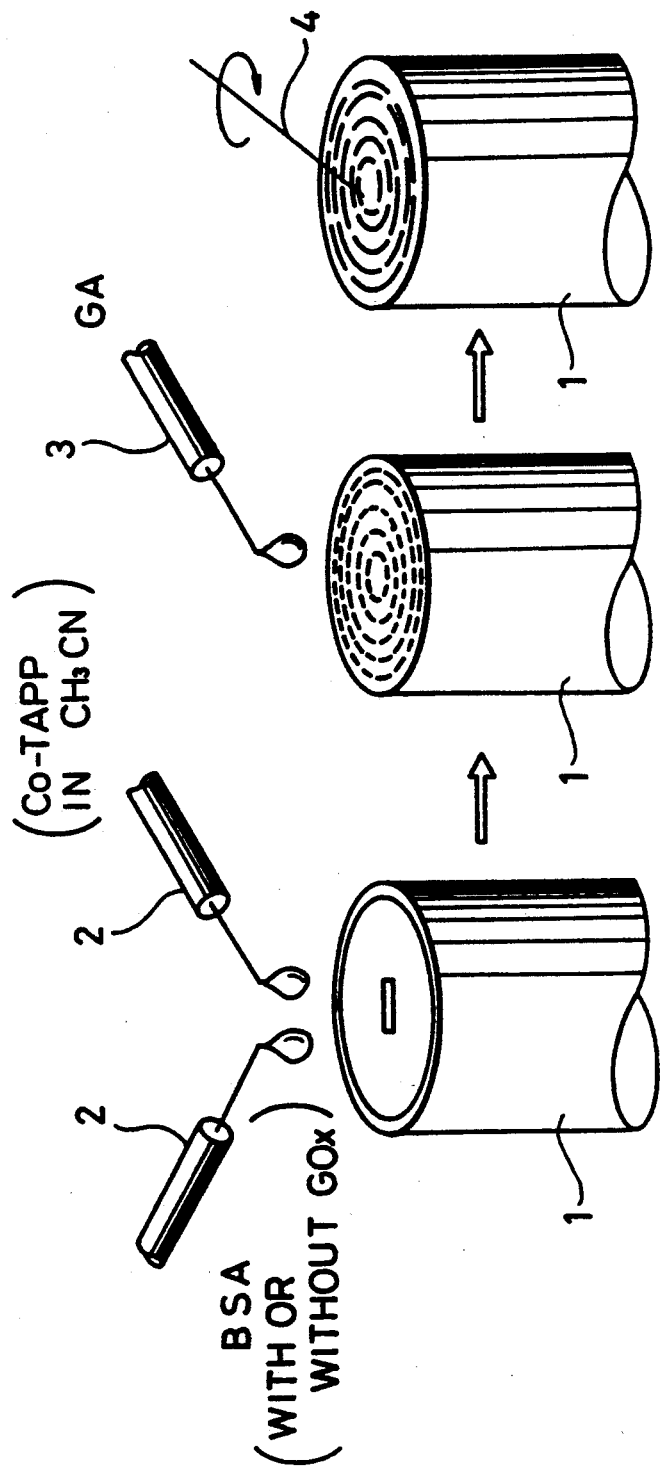

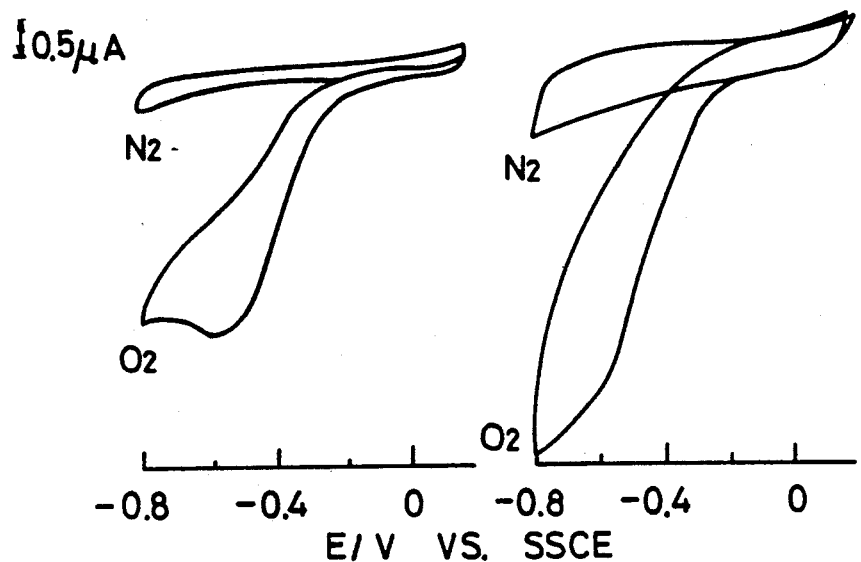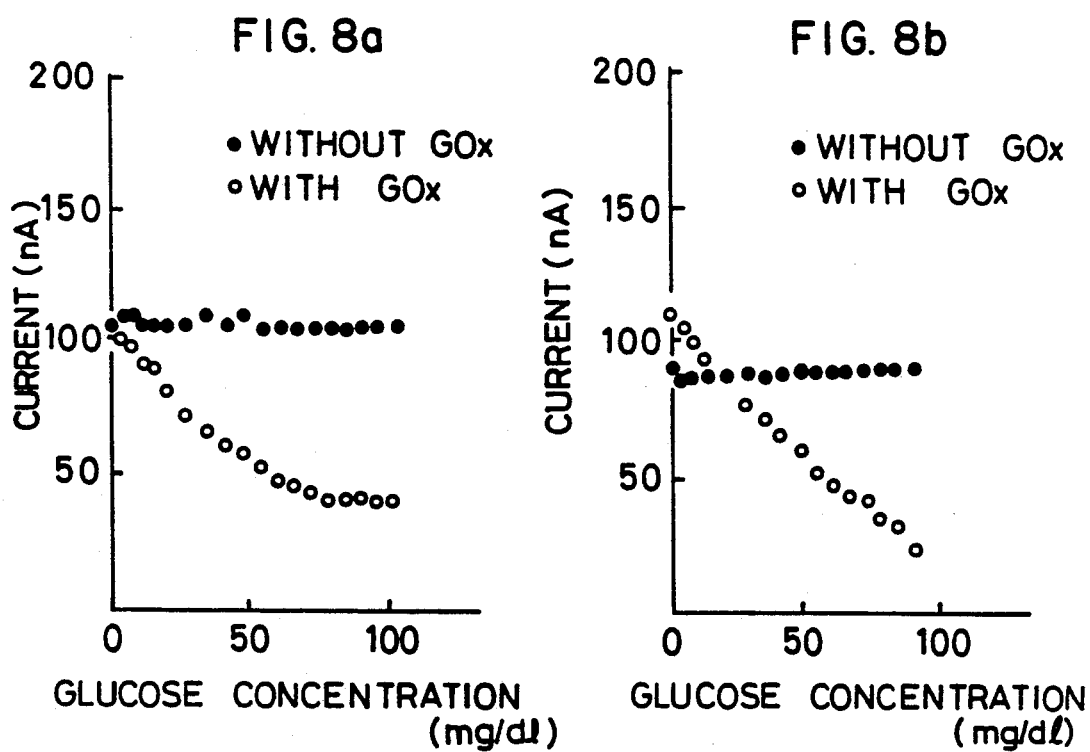

ENZYME SENSOR AND METHOD OF MANUFACTURING THE SAME

BACKGROUND OF THE INVENTION

1. Field of the Invention

This invention relates to an enzyme sensor for measuring the concentration of biological substrate with an amperometric method using an enzyme electrode and, more particularly, to an enzyme sensor utilizing a reducing catalytic action of di-valent iron ions structurally introduced in a thin film of clay (i.e., montmorillonite).

More specifically, the invention concerns an enzyme sensor using an enzyme electrode and a method of manufacturing the same and, more particularly, an enzyme sensor for measuring the concentration of substance under measurement by detecting a change oxidation/reduction response current which is proportional to the quantity of oxygen ($O_2$) consumed by enzymic reaction and a method of manufacturing the same.

2. Description of the Prior Art

Enzyme sensors are well known as biological sensors. They are utilized mainly for clinical chemical analysis, and among them are those, which are in practical use for glucose in blood, urea and neutral and phospholipids as substrate under measurement.

For example, in case of glucose as subject of measurement an enzymic reaction takes place as follows.

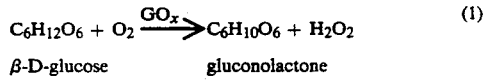

$$\beta\text{-D-glucose} \qquad \text{gluconolactone} \tag{1}$$

This means that $\beta$-D-glucose consumes oxygen ($O_2$) by the action of $\beta$-D-glucose oxidase ($GO_x$), thus producing organic acid (gluconolactone) and hydrogen peroxide ($H_2O_2$). Therefore, the concentration of glucose can be measured from the quantity of generated hydrogen peroxide or gluconolactone.

When measuring the glucose concentration from the quantity of generated hydrogen peroxide, the generated hydrogen peroxide is oxidized with a metal electrode, and the oxidation current is measured. Alternatively, the generated hydrogen peroxide is reduced, and the reduction current is measured. However, the oxidation or reduction current is influenced by oxygen, or with a prior art sensor electrode it is liable to be influenced by a change in the surface state of the electrode. Further, in the principle of measurement by electrochemical method the sensor construction consists of electrode substrate, liquid, enzyme-fixed film and liquid under test, and miniaturization of the sensor is difficult due to the liquid present between the electrode and film.

There are further prior art methods of measurement, that is, (1) one, in which hydrogen peroxide is decomposed with catalase into oxygen and water, and the quantity of resultant oxygen is measured, and (2) one, in which iodide ions are oxidized in the presence of peroxidase or an inorganic catalyst (e.g., molybdenum), the quantity of iodine is measured by causing a reaction

$$H_2O_2 + 2I^- + 2H^+ \xrightarrow{\text{peroxidase}} I_2 + 2H_2O \tag{2}$$

and indirectly measuring the quantity of hydrogen peroxide.

As shown above, in any prior art method of measuring the quantity of glucose from the quantity of generated hydrogen peroxide, the quantity of consumed oxygen or generated iodine is measured, and the quantity of generated hydrogen peroxide, is determined indirectly from the measured quantity.

In such method of measurement, which involves two reaction stages, an electrode for measuring oxygen or iodine is necessary in addition to an enzymic electrode for decomposing glucose or the like into hydrogen peroxide. In addition, the measurement is very cumbersome and requires a long time.

Further, since in the prior art electrochemical method the sensor includes inner liquid, contamination of the liquid under test is liable, and also miniaturization of the sensor is difficult.

Meanwhile, a sensor part of the enzyme sensor for measuring the concentration of glucose in blood through measurement of the consumption of oxygen generated in enzymic reaction mostly uses a commonly termed Clark type oxygen electrode, which uses platinum as cathode and silver/silver chloride as anode and has chloride-added standard buffer solution as sealed inner liquid and an outer cover film selectively permeable to oxygen gas.

However, the Clark type oxygen electrode can be miniaturized with difficulty. In addition, since it has an inner solution chamber, it is subject to leakage and contamination. Further, the response speed is slow. Still further, while quick response can be obtained with a separate type oxygen electrode, a cathode type platinum electrode is subject to influence of $H^+$ ion concentration. For this reason, with a fluid system subject to great pH changes distinction with true oxygen partial pressure ($PO_2$) concentration is difficult.

SUMMARY OF THE INVENTION

This invention has been intended in the light of the above, and its object is to provide an enzyme sensor, which can measure the concentration of biological substrate such as glucose simply and in a short period of time, can be readily miniaturized, is free from contamination problems, is free from influence of $H^+$ ion concentration and oxygen partial pressure, has improved response speed and is suitable for continuous monitoring measurement in fluid system, as well as a method of manufacturing the same.

To attain the above object of the invention, there is provided as a first principle thereof an enzyme sensor, which comprises an electrically conductive substrate, a reduction function layer covering at least part of the electrically conductive substrate, including a compound containing an electron movement medium and divalent iron ions and capable of producing a reduction reaction of hydrogen peroxide and an enzyme-fixed layer covering at least part of the reduction function layer.

The electron movement medium n has a structural formula of $[ML_mY_n]$ (where M represents a transition metal ion, L and Y represent compounds coordinated in the transition metal ion and m and n represent coordination numbers) and is specifically expressed as $[Ru(NH_3)_6]^{3+}$ or, $[Ru(NH_3)_5X]$ (where X represents pyridine, halogen, nicotinamide or crystal water). The enzyme sensor according to the invention utilizes a reducing catalytic reaction caused by movement of electrons in the reduction function layer. It has a composite structure as shown in FIG. 1, which is obtained by causing substitution between sodium salt contained in clay (i.e., sodium salt montmorillonite) and $[Ru(NH_3)_6]^{3+}$ complex to apparently fix $[Ru(NH_3)_6]^{3+}$ in the clay layer and covering the resultant substrate with an enzyme-fixed layer. Therefore, when the sensor is touched by glucose liquid, hydrogen peroxide having been produced by oxidation reaction of glucose as shown in FIG. 1 is reduced to water by divalent iron ions structurally taken in the clay layer. Consequently, reduction current is produced in the electrically conductive substrate. This current is proportional to the concentration of glucose. Thus, the concentration of glucose can be measured by measuring the current value. In FIG. 1, a circle mark represents an oxygen atom, a double circle mark represents a hydrogen atom, and black circle mark represents a magnesium or silicon or aluminum atom.

FIG. 2 is a schematic illustration of the principle of measurement of the glucose concentration based on oxidation reaction of glucose in the enzyme-fixed layer and catalytic reduction reaction of $[Ru(NH_3)_6]^{3+}$ complex and divalent iron ions in the reduction function layer.

The concentration of enzyme is measured by using an amperometric method, and the reduction current can be varied by varying X in the formula representing $[Ru(NH_3)_6]^{3+}$ complex.

The enzyme sensor according to the first principle of the invention has a two-layer solid-film structure consisting essentially of a reduction function layer including a compound containing an electron movement medium and divalent iron ions and an enzyme-fixed film covering the reduction function layer, and in which hydrogen peroxide generated as a result of decomposition of glucose or the like in the enzyme-fixed film is reduced by the electron movement medium and divalent iron ions in the reduction function layer. Thus, a simplified construction can be obtained, and measurement can be extremely facilitated. Further, it is possible to reduce the time for measurement. Further, since the enzyme-fixed layer can be formed by an electrolytic reaction method, a dipping method, a spin coating method or the like, the coating film can be formed even if the electrode substrate is very small in size. Besides, the sensor has a solid electrode structure and, unlike the prior art sensor, does not require any inner solution chamber. Thus, there is no problem of contamination of liquid under measurement. Further, it is possible to manufacture a super-miniaturization sensor. The utility of the sensor is thus extremely elevated particularly in the medical field.

According to a second principle of the invention, there is provided an enzyme sensor, which comprises an electrically conductive substrate, an oxygen electrode layer covering the substrate and containing a ligand compound having an oxygen-reducing catalytic function and an enzyme-fixed layer covering the oxygen electrode layer.

This structure, which is of solid type, is free from such problems as leakage and contamination as in the prior art sensor. Further, the miniaturization (to 0.01 $cm^2$ or less) can be readily obtained, and the sensor is less influenced by the $H^+$ ion concentration and permits accurate measurement even when it is used for a fluid system subject to great pH variations.

The ligand compound having oxygen-reducing catalytic function suitably consists essentially of a cyclic nitrogen-containing compound, and is particularly suitably a porphyrin derivative, phthalocyanine derivative, cyclam derivative or phenanthroline derivative.

As porphyrin derivative may be used mesotetra(O-aminophenyl) cobalt porphyrin. As phthalocyanine derivative may be used tetraaminophthalocyanine, and as phenanthroline derivative may be used diaminophenanthrene.

The transition metal taken in the ligand compound may be any one having the oxygen-reducing catalytic function such as cobalt, iron, nickel, chromium, molybdenum and ruthenium.

Further, the electrically conductive substrate suitably consists essentially of a material influenced by neither oxygen concentration nor $H^+$ ion concentration, for instance electrically conductive carbon material.

The enzyme sensor noted above may be manufactured by forming the oxygen electrode layer by coating the electrically conductive substrate with a solution containing a ligand composition having an oxygen-reducing catalytic function and then forming the enzyme-fixed layer by coating the oxygen electrode layer with a fixing reagent containing enzyme.

The oxygen electrode layer may be manufactured by a dropping method or a resist method as well as the coating method noted above. Further, it is possible to polymerize $NH_2$ radical, OH radical, COOH radical, vinyl radical, etc. coupled to the outer core of the ligand compound (into pendant polymer, ladder polymer, vinyl polymer, etc.) by means of electrolytic polymerization or vacuum evaporation.

Further, it is possible to have a ligand compound having the oxygen-reducing catalytic function be contained together with enzyme in the same layer and fix it therein together with enzyme in an insoluble form. Again in this case it is possible to obtain the same effect as the sensor.

The enzyme sensor can be manufactured by dropping or coating a solution containing a ligand compound having the oxygen-reducing catalytic function, a solution containing enzyme and a fixing reagent in the mentioned order on the surface of an electrically conductive substrate for mixing and reacting these substances, thereby fixing the ligand together with enzyme in an insoluble form.

With the enzyme sensor according to the second principle of the invention, the electrically conductive substrate such as conductive carbon is covered by the oxygen-reducing catalytic function layer and the enzyme layer. Thus, unlike the prior art enzyme sensor, there is no problem of contamination. In addition, ready manufacture and miniaturization of the sensor are possible. The response speed thus can be greatly increased, there is no influence of the $H^+$ ion concentration or the like, and highly accurate measurement can be obtained even in the fluid system.

Further, where an electrically conductive substrate is covered by a layer containing an oxygen-reducing catalytic substance enzyme in a mixed state, the manufacture is further facilitated, and super-miniaturization is simplified. Further, substrate permeability control and response speed control can be readily obtained by varying the ratio between the catalytic substance and enzyme. Further, with the method of manufacturing enzyme sensor according to the invention, it is possible to readily manufacture an enzyme sensor.

BRIEF DESCRIPTION OF THE DRAWINGS

FIGS. 6(a) to 6(c) are perspective views showing a method of manufacturing an enzyme sensor as Embodiment 2 of the invention;

FIGS. 7(a) and 7(b) are graphs showing cyclic voltamograms of sensors manufactured by the method illustrated in FIGS. 6(a) to 6(c), FIG. 7(a) showing a characteristic of electrode A not containing glucose oxidase, and FIG. 7(b) showing a characteristic of electrode B containing glucose oxidase;

FIGS. 8(a) and 8(b) are views showing changes in current corresponding to glucose concentration of electrode B, with FIG. 8(a) being a characteristic diagram obtained four days after manufacture, and FIG. 8(b) being a characteristic diagram obtained 20 days after manufacture;

DESCRIPTION OF THE PREFERRED EMBODIMENTS

Figure 1:
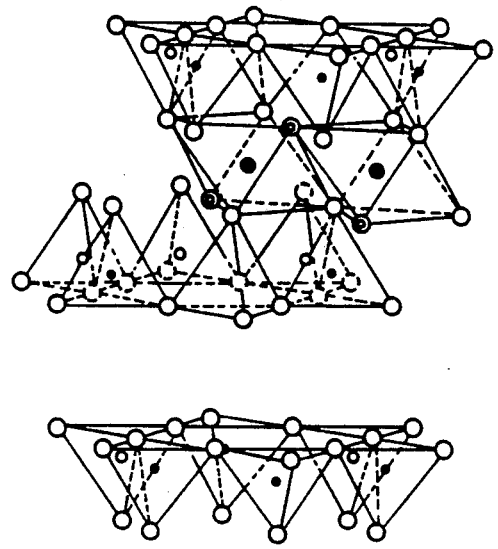
FIG. 1 is a view showing the structure of montmorillonite used for enzyme sensor according to the invention.
Figure 2:
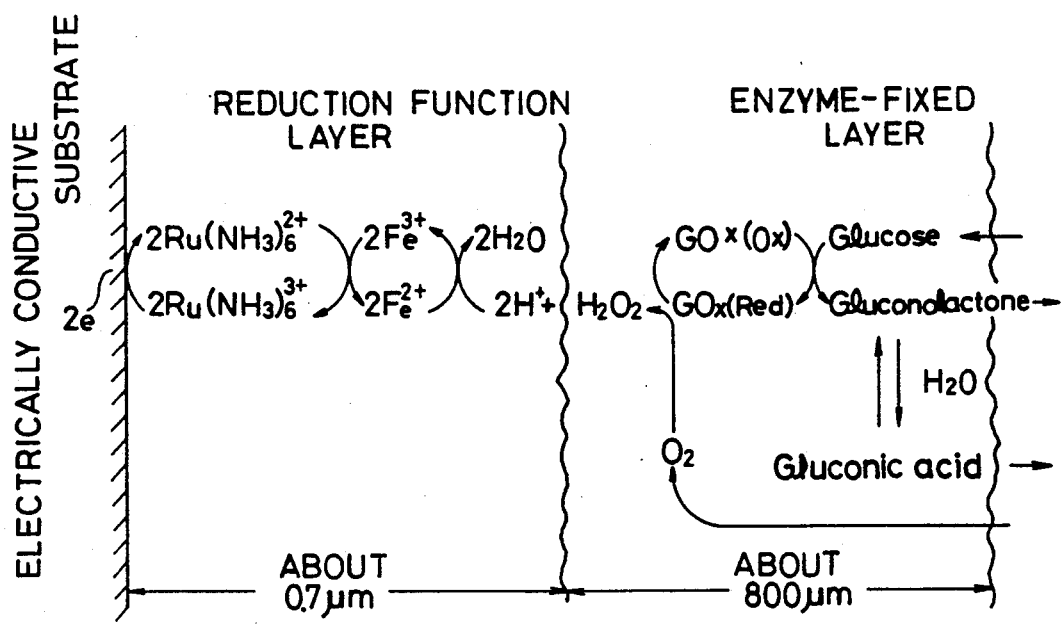
FIG. 2 is a schematic view showing the principle of the enzyme sensor according to the invention.

Now, an embodiment of the enzyme sensor according to a first principle of the invention will be described in detail with reference to the drawings.

EMBODIMENT 1

Electrically conductive carbon such as basal-plane pyrolytic graphite (hereafter referred to as "BPG" and manufactured by UCC Co., Ltd.) was cut to a cylindrical form with a diameter of about 1 mm. A copper lead wire was bonded with silver paste to one end surface of the carbon cylinder thus obtained, the peripheral surface of the carbon cylinder was secured with a thermally shrinkable tube (a Teflon tube provided under a trade mark "PENNTUBE WTH" manufactured by Penject Co., Ltd.), and the gap was filled with an insulating epoxy resin ("TB2067" manufactured by Three Bond Co., Ltd.), which was then thermally solidified to produce a carbon electrode.

Then, this carbon electrode was coated with a montmorillonite solution (with a concentration of 0.5% by weight) to a thickness of about 1 micron. This electrode was immersed in a blend solution of 0.1 M phosphate buffer solution (pH+7.00) containing 0.2 mM [Ru(NH$_3$)$_6$]$^{3+}$ complex after drying it (to prevent generation of cracks if it was dried perfectly). The solution was made under nitrogen atmosphere, and potential sweeping was performed in a range of +0.2 to −0.6 V (vs. saturated sodium chloride calomel electrode:SSCE) to let [Ru(NH$_3$)$_6$]$^{3+}$ complex be taken in the clay (for 5 minutes).

After drying the carbon electrode, enzyme solution was dropped onto the electrode with microsyringe and spread uniformly to cause a bridging reaction, thus fixing the enzyme.

The enzyme solution was as follows.

a) 4 mg/ml glucose oxidase (GOx) plus 15% bovine blood serum albumin and 50 mM phosphate buffer solution (pH=7.00)—1.0 μl b) 25 wt % glutaric aldehyde solution—1.2 μl Then, the system was dipped in 0.1 M phosphate buffer solution (pH=7.00) containing 5×10$^{-2}$ mM [Ru(NH$_3$)$_6$]$^{3+}$ complex for 15 minutes, and then it was dipped in 10 wt % glycine solution for 2 minutes to remove non-reacted glucose oxidase.

EXPERIMENTAL EXAMPLE 1

Experiments for measuring the glucose concentration was conducted. More specifically, a blend solution of 0.1 M phosphate buffer solution containing 1.6×10$^{-2}$ M [Ru(NH$_3$)$_6$]$^{3+}$ complex was charged into a cell (with a volume of 25 milliliters), and it was sufficiently substituted using nitrogen gas. Then the concentration of glucose was measured by a constant potential current process using a three-electrode cell consisting of an active electrode, an opposing electrode (platinum net) and a reference electrode (saturated sodium chloride calomel electrode:SSCE). This was done by measuring reduction current (substantially saturation reduction current of 95% or above) under a condition of a constant potential (−0.18 V vs. SSCE).

EXPERIMENTAL EXAMPLE 2

Cyclic voltammetry was conducted by constructing the three-electrode structure mentioned in Experimental example 1 by using an enzyme sensor produced in Embodiment 1 and comprising electrically conductive carbon, a clay layer (1 micron thick) and enzyme-fixed film (0.3 micron thick).

Figure 3:
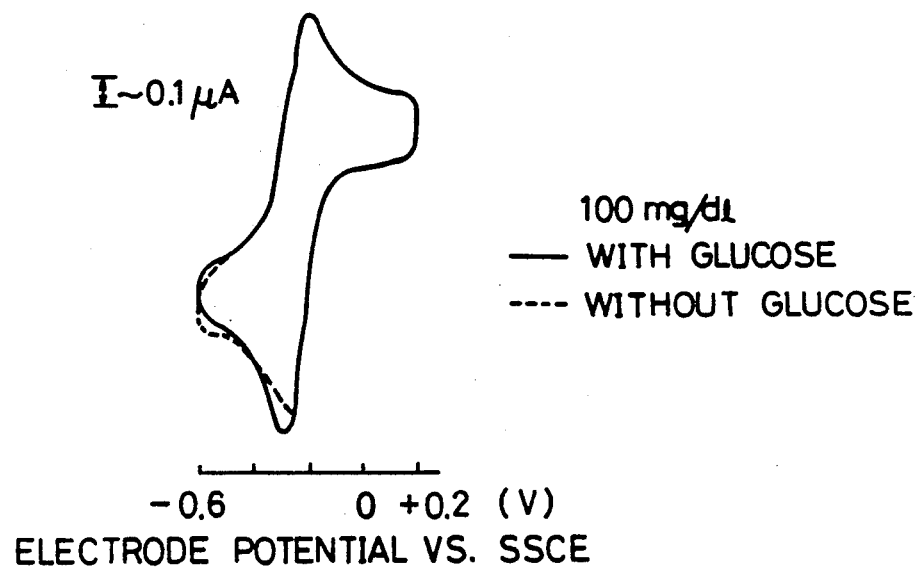
FIG. 3 is a view showing a cyclic voltamogram of an enzyme sensor as Embodiment 1 of the invention.

The experiment was conducted by using as liquid under measurement a blend solution of a phosphate buffer solution (pH=7.00) containing 1.16×10$^{-2}$ mM [Ru(NH$_3$)$_6$]$^{3+}$ complex, and the applied voltage was swept between −0.6 and 0.2 V (vs. SSCE) at a sweeping rate of 200 mV/sec. FIG. 3 shows a cyclic voltamogram obtained by this experiment. The waveform and an oxidation peak potential of −0.2 V (vs. SSCE) and reduction peak potential of −0.27 V (vs. SSCE) show that the oxidation/reduction reaction of the complex is reversible.

Then, glucose was added to the system, and hydrogen peroxide generated by the action of glucose oxidase was reduced with the surface of clay as electrode cover layer. The reduction current at this time was obtained (but the potential being constant at −0.18 V (vs. SSCE) at this time). The measurement was carried out in oxygen atmosphere.

Figure 4A:
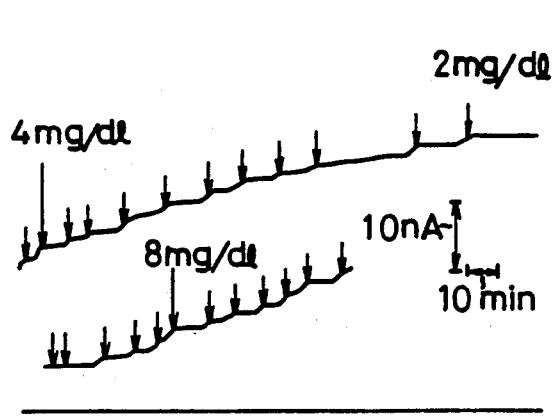
FIGS. 4(a) and 4(b) are graphs showing changes in current corresponding to glucose concentration in the same embodiment.
Figure 4B:
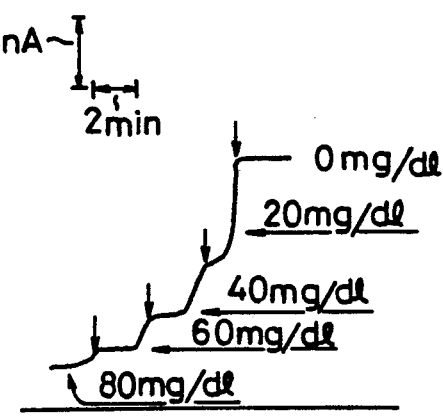
Figure 5:
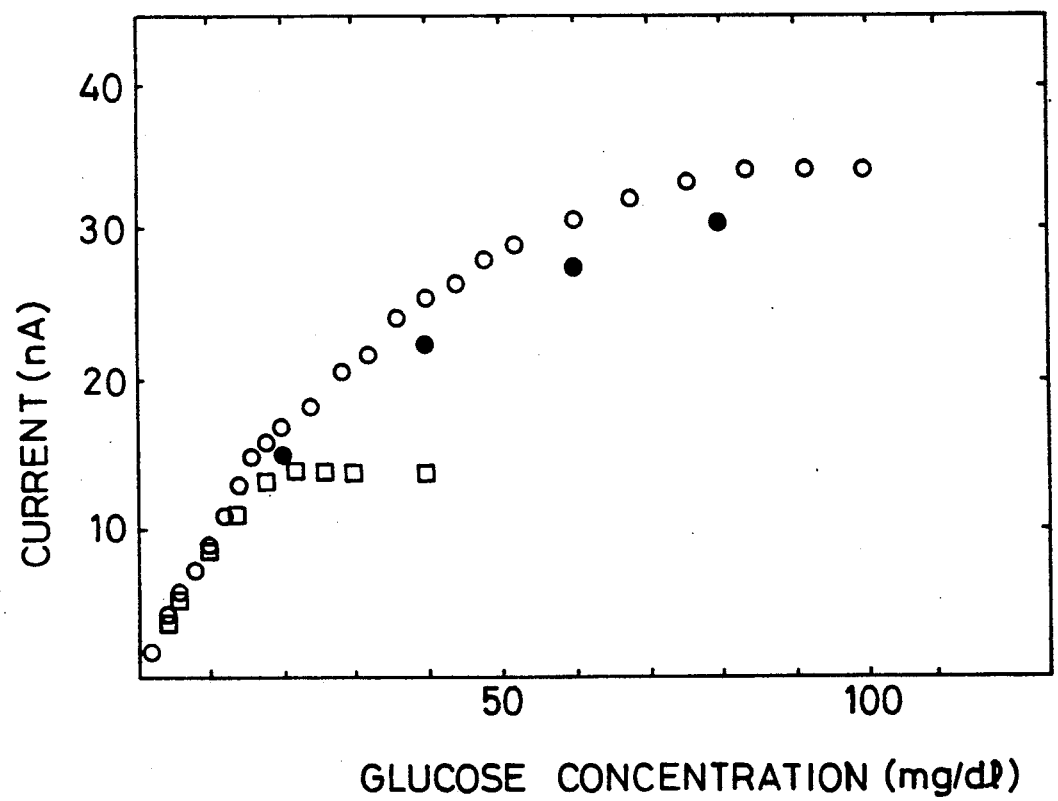
FIG. 5 is a view showing the relation between glucose concentration and current based on characteristic values shown in FIG. 4.

FIGS. 4(a) and 4(b) show changes in current corresponding to changes in the glucose concentration (2 to 80 mg/dl). FIG. 5 shows the relation between the glucose concentration and current at this time. In FIG. 5, a circle mark corresponds to FIG. 4(a), a black circle mark corresponds to FIG. 4(b), and a square mark corresponds to measurement in air atmosphere.

Results of measurement show that in the oxygen atmosphere the relation between the concentration and reducing current is substantially linear up to a glucose concentration near 50 mg/dl. Meanwhile, it was shown that in the measurement carried out in air atmosphere the current value reached saturation when the glucose concentration exceeded about 20 mg/dl.

When the reduction current was measured by holding a constant potential of $-0.27$ V (vs. SSCE), the reduction current was shown in the reducing direction with respect to time. Therefore, in this experiment the response potential to the reduction current of hydrogen peroxide with which the reduction current is generated in proportion to the reaction of glucose decomposition, was selected to $-0.18$ V (vs. SSCE).

From the above it was made obvious that glucose concentration can be measured by reducing hydrogen peroxide generated with the enzyme reaction of glucose oxidase with clay (sodium salt montmorillonite) containing $[Ru(NH_3)_6]^{2+}$ complex.

Now, an embodiment of the enzyme sensor according to a second principle of the invention will be described in detail with reference to the drawings.

EMBODIMENT 2

A cylindrical or disk-like substrate (0.525 mm in diameter) consisting of an electrically conductive carbon material (BPG manufactured by UCC Co., Ltd.) was prepared. A lead wire was connected to one end of the substrate with an electric conductive adhesive, the substrate was covered with an insulating Teflon tube, and the gap was filled for electric insulation with an insulating adhesive (Three Bond Co. Ltd., TB2067), thus producing a capillary electrode. This capillary electrode was cut at an end portion to produce a minute carbon disk type electrode substrate 1 as shown in FIG. 6(a). Two electrodes 1 were prepared, and the following solutions (A) and (B) were dropped with microsyringe 2 on these electrodes and mixed with needle tips.

(A) 2.4 microliters of 5 mM mesotetra (O-aminophenyl) cobalt porphyrin (Co-TAPP) (in CH₃CN (solvent)) plus 2.0 microliters of 50 mM phosphate buffer solution containing 15% bovine blood serum albumin (BSA)

(B) 2.4 microliters of 5 mM mesotetra (O-aminophenyl) cobalt porphyrin (Co-TAPP) (in CH₃CN (solvent)) plus 2.0 microliter of 50 mM phosphate buffer solution containing 0.2 mg/ml glucose oxidase (GO$_x$) and 15% bovine blood serum albumin (BSA)

Then, as shown in FIG. 6(b), 1.2 microliters of 25 wt % glutaraldehyde was dropped with a microsyringe 3, and these solutions were uniformly mixed again with a needle tip 4 as shown in FIG. 6(c) and reacted in atmosphere for 15 minutes. Then, the system was reacted in 10 mM phosphate buffer solution (pH=7.0) for 12 hours, and then it was held dipped in 10 wt % glycine aqueous solution for 5 minutes to remove non-reacted glutaladehyde.

EXPERIMENTAL EXAMPLE 3

Cyclic voltamogram with respect to oxygen concentration in 10 mM phosphate buffer solution (pH=7.0) was obtained by using an enzyme electrode manufactured by Embodiment 2.

FIG. 7(a) shows results with electrode A not containing any glucose oxidase (GO$_x$), and FIG. 7(b) shows results with electrode B containing glucose oxidase. As a result, it was made obvious that at a constant potential ($-0.8$ V vs. saturated sodium chloride calomel electrode (SSCE) current changes are greater with electrode B containing glucose oxidase than with electrode A.

Further, the current density (A/cm$^2$) was $2.12 \times 10^{-3}$ A/cm$^2$ with electrode A. That is, with electrode B it was 1.58 times that of electrode a.

EXPERIMENTAL EXAMPLE 4

Current changes corresponding to glucose concentration were studied using electrode B containing glucose oxidase in Experimental example 3 and electrode A not containing glucose oxidase.

In the experiment, 1 g/dl of glucose solution was added to 10 mM phosphate buffer solution (pH=7.00), then air bubbling (at a speed of 0.2 liter/min.) was carried out, then the system was stirred with a stirrer, and current changes at a constant potential ($-0.6$ V vs. SSCE) were examined. FIGS. 8(a) and 8(b) show results. More specifically, FIG. 8(a) shows results four days after manufacture, and FIG. 8(b) shows results 20 days after manufacture.

It was thus found that a satisfactory enzyme sensor could be obtained, with which for a glucose concentration range of 5 to 100 mg/dl changed linearly from about 100 to about 39.29 nA with electrode four days after manufacture and from about 110 to 33.3 nA with electrode 20 days after manufacture.

EMBODIMENT 3

An enzyme electrode containing glucose oxidase was manufactured in the same way as in Embodiment 2 except for that the concentration of mesotetra (O-aminophenyl) cobalt porphyrin was changed to 10 mM.

EXPERIMENTAL EXAMPLE 5

With the electrode manufactured in Embodiment 3, current changes with respect to glucose concentration (5 to 100 mg/dl) were measured 20 days afterwards in the same manner as in Experimental example 4. As a result, it was found that a satisfactory enzyme sensor could be manufactured with current changed linearly in a range of 110 to 10 nA. The current density was $1.62 \times 10^{-3}$ A/cm$^2$ at constant potential ($-0.8$ V vs. SSCE).

EMBODIMENT 4

One end of a carbon fiber (with a sectional area of $7.85 \times 10^{-7}$ cm$^2$) was connected to a lead wire using an electrically conductive adhesive and inserted into a glass capillary with a thinly elongated end portion, and the gap was filled for electric insulation with an insulating adhesive to obtain a capillary electrode. This capillary electrode was cut to remove an end portion and polished to manufacture a super-minute disk type carbon fiber electrode.

Then, three electrode type electrolytic polymerization was brought about using a saturated sodium chloride calomel electrode (SSCE), a platinum wire as back electrode, and a carbon fiber electrode as acting electrode. The electrolyte used for the experiment consisted of 2.4 microliters of 1 mM mesotetra (O-aminophenyl) cobalt porphyrin (Co-TAPP) (in CH₃CN (solvent) and 0.1 M NaClO₄ (in CH₃CN), and potential sweeping at a speed of 50 mV/sec. was carried out three times with a potential range of 0 to 1.8 V (vs. SSCE). Thereafter, constant potential electrolysis was carried out for 10 minutes at 1.8 V, thus covering the carbon fiber electrode with an electrolytic polymerization layer with a thickness of about 0.5 micron.

Then, the film electrode was dipped in a phosphoric acid buffer solution (pH=8.00) containing 100 mg/ml glucose oxidase and 15 wt % bovine blood serum albumin and dried. The dipping and drying were repeatedly carried out about five times, and then a bridging reaction was caused at an interval of 12 hours in vapor of 50% glutaraldehyde (GA) solution to fix glucose oxidase. Afterwards, non-reacted glutaraldehyde was washed away using 20% glycine solution, thus producing an enzyme electrode. The electrode was then dipped in a methanol-DMF (dimethylformamide) of 0.5% polyhexaethylmethacrylate (P-HEMA) to form a protective cover layer with a thickness of about 30 microns.

EXPERIMENTAL EXAMPLE 6

50 mM phosphate buffer solution containing 18 mg/dl glucose solution was dropped onto the enzyme sensor obtained in Embodiment 4, and the response speed at this time was examined in nitrogen, air and oxygen atmospheres.

Figure 9:
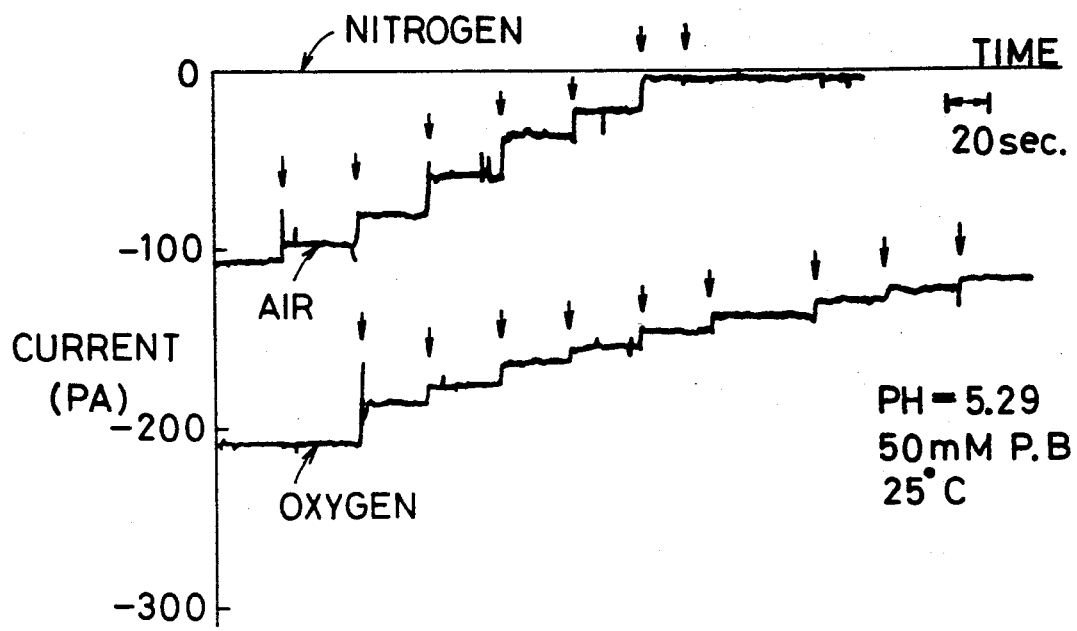
FIG. 9 is a graph showing a response characteristic of enzyme sensor to glucose in Embodiment 4.
Figure 10:
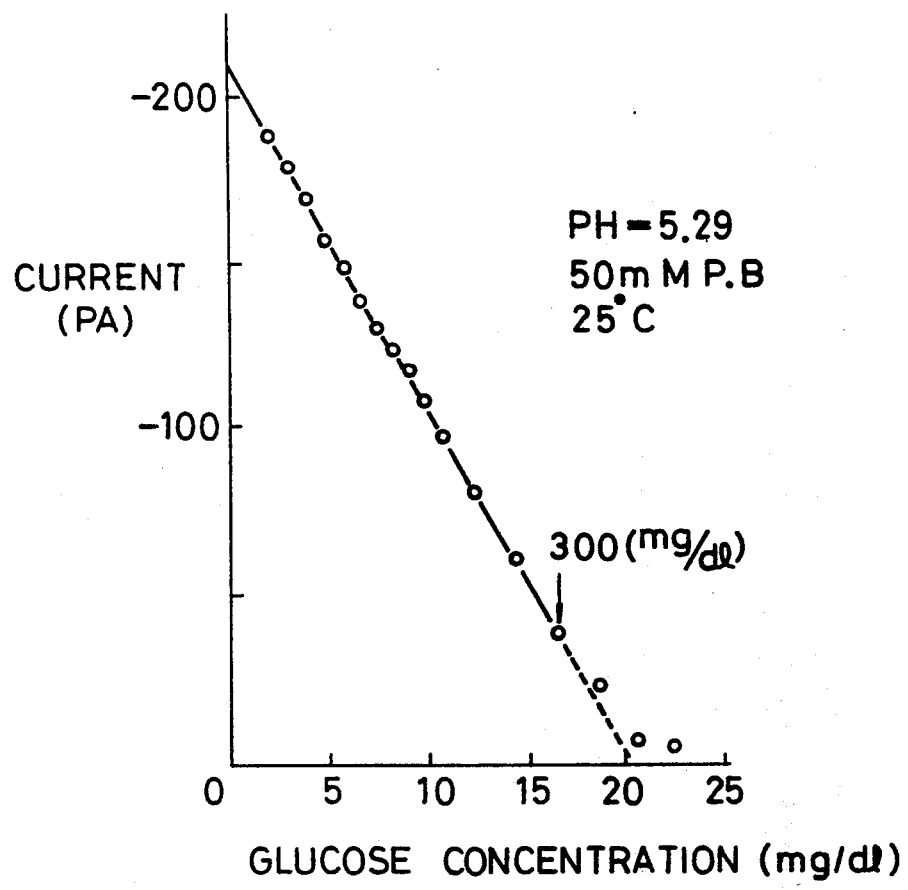
FIG. 10 is a graph showing a relation between glucose concentration and current based on the characteristic shown in FIG. 9.

FIG. 9 shows results. The response speed was several seconds. Current changes were obtained at a constant potential of −0.6 V with respect to saturated sodium chloride calomel electrode (SSCE). The current with respect to glucose concentration changed linearly in a range of about −200 to about −10 pA with a glucose concentration range of 2 to 22 mM (36 to 396 mg/dl as shown in FIG. 10).

EMBODIMENT 5

Figure 11:
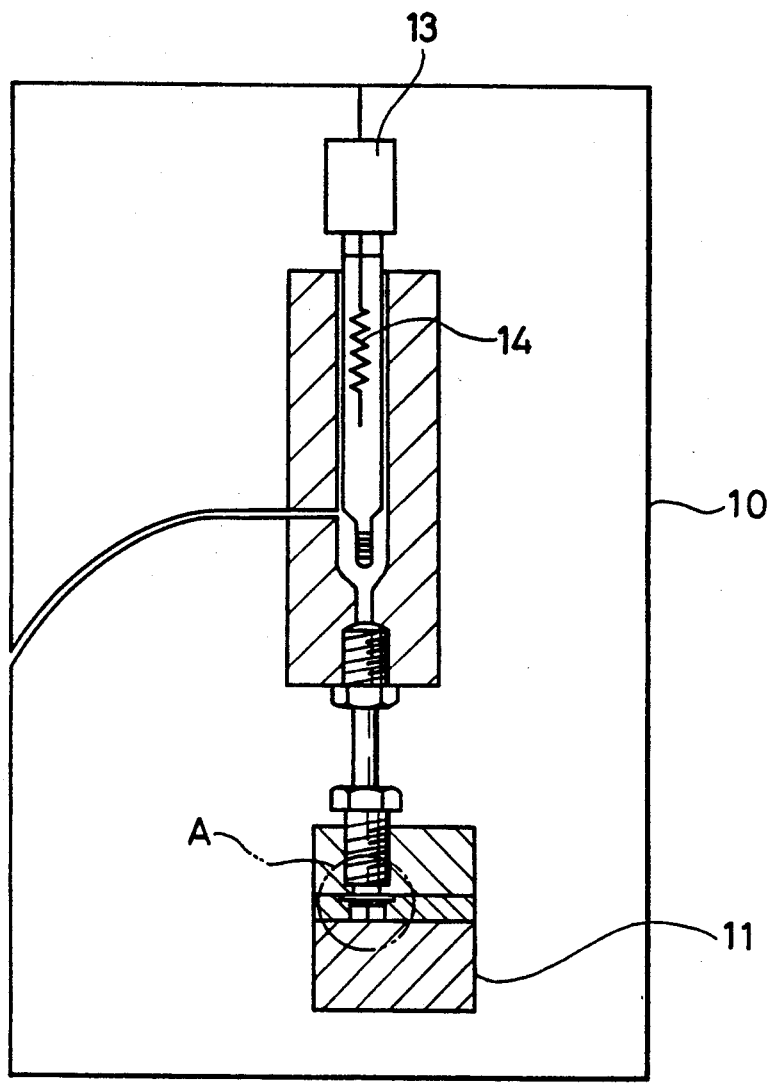
FIG. 11 is a sectional view showing the schematic construction of the apparatus used in Embodiment 5.
Figure 12:
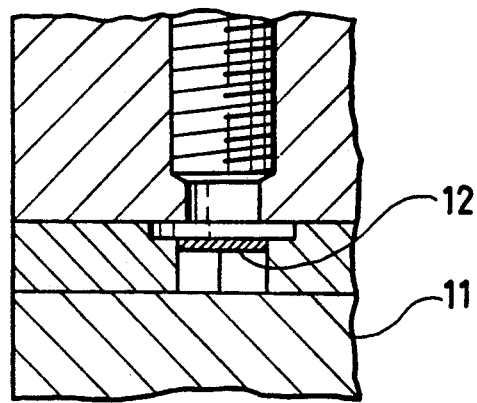
FIG. 12 is a sectional view, to an enlarged scale, showing a portion shown in FIG. 11.

Two cobalt porphyrin electrolytic polymerization thin layers were formed under the following conditions on the acting electrode 11 of EC-detector (Model-LC-4B) 10 (which had a size of 30 mm by 30 mm by 5 mm, and included an embedded glassy carbon electrode 12 having diameter of 3 mm in it, manufactured by Bioanalytical Co., Ltd. (Japan sales office: Bioanalytical System Inc., B.A.S.), as shown in FIGS. 11 and 12 for using it for commonly called flow injection analysis for monitoring current generated by causing reaction of an active substance (i.e., $O_2$ according to the invention) in the substance under test on the surface of dual acting electrode in a thin layer cell. FIG. 12 is an enlarged-scale view showing portion A in FIG. 11.

Using a three-electrode cell having glassy carbon electrode 12 as acting electrode, a commercially available silver/silver chloride electrode as reference electrode 13 and platinum wiring as back electrode 14, potential sweeping was carried out twice in an electrolyte having the following composition, in a range of 0.0 to +1.8 V (vs. SSCE) and at a sweep speed of 50 mV/sec.), thus completing a cover layer.

2.4 microliters of 1 mM mesotetra (O-aminophenyl) cobalt porphyrin (Co-TAPP) (in $CH_3CN$ (solvent)), 0.1 M $NaClO_4$ (in $CH_3CN$)

In this way, a polymesotetra (O-aminophenyl) cobalt porphyrin layer having a thickness of about 0.1 μm was obtained.

EMBODIMENT 6

The surface of the carbon electrode/polymesotetra (O-aminophenyl) cobalt porphyrin electrode manufactured in Embodiment 5 was covered with an enzyme-fixed layer as follows. The electrode in Embodiment 5 was dipped in a solution obtained by dissolving 100 mg/ml of glucose oxidase and 15 wt % of bovine serum albumin in phosphate buffer solution (pH=8.0) and then dried. This operation was repeatedly carried out about five times. Subsequently, a bridging reaction is brought about with 50% glutaraldehyde solution to fix glucose oxidase, and then non-reacted substance was washed away with 20% glycine solution. In this way, an enzyme-fixed layer having a thickness of about several ten microns was covered, and a structure comprising carbon electrode, polymesotetra (O-aminophenyl) cobalt porphyrin thin layer and enzyme-fixed layer was obtained.

EXPERIMENTAL EXAMPLES 7 TO 9

Current characteristics were studied by using the double-layer-covered electrode consisting of the polymesotetra (O-aminophenyl) cobalt porphyrin thin layer and enzyme fixed layer electrode of Embodiment 6 as acting electrode (glassy carbon electrode with a diameter of 3 mm and electrode area of $7.065 \times 10^{-2}$ $cm^2$) and silver/silver chloride electrode as reference electrode in a flow injection analysis apparatus. Experiment conditions were:

1) Current changes at constant potential of 0.4 V (vs. silver/silver chloride)
2) Carrier solution: 50 mM phosphate buffer solution (pH=7.0)
3) Injected solution: 20 microliters (fixed amount) of 100 mg/dl glucose.

The reproducibility of flow rate changes was studied with respect to three flow rates of 1, 1.5 and 0.5 ml/min. As a result, it was found that flow injection analysis could be carried out accurately.

In this embodiment a disk electrode was used as an electrically conductive substrate. However, this is by no means limitative, and it is possible to use minute band electrodes, array electrodes or cylindrical or groove-like electrodes.

While in this embodiment glucose oxidase, is shown the invention is applicable as well to substances produced with oxygen as the receptive substance and hydrogen peroxide as the reaction product such as enzyme, glucolate oxidase, malate oxidase, hexose oxidase, cholesterol oxidase, allyl-alcohol oxidase, L-gluconolactone oxidase, galactose oxidase, Pyranose oxidase, L-sorbose oxidase, pyridoxine 4-oxidase, alcohol oxidase, pyruvate oxidase, oxylate oxidase, glyoxylate oxidase, dihydroorotate oxidase, rathosterol oxidase, D-aspartate oxidase, D-amino acid oxidase, L-amino acid oxidase, amine oxidase, D-glutamic acid oxidase, L-glutamic acid oxidase, ethanolamine oxidase, tyramine oxidase, putrecine oxidase, cyclohexylamine oxidase, L-ricin α-oxidase, N-methylamino acid oxidase, $N^6$-methylrycine oxidase, 6-hydroxy-D-nicotine oxidase, dimethyl-glycine oxidase, nitroethane oxidase and sulphite oxidase.

What is claimed is:

1. An enzyme sensor comprising:
   an electrically conductive substrate;
   a reduction function layer covering at least part of said electrically conductive substrate, including an electron movement medium with a structure represented as $[Ru(NH_3)_6]^{3+}$ or $[Ru(NH_3)_5X]$, where X represents pyridine, halogen ion, nicotinamide or crystal water, and di-valent iron ions, and capable of causing a reduction reaction of hydrogen peroxide; and an enzyme-fixed layer covering at least part of said reduction function layer.

2. An enzyme sensor comprising:
an electrically conductive substrate comprising a carbon fiber with a sectional area of $7.85 \times 10^{-7}$ cm$^2$,
an oxygen electrode layer covering said electrically conductive substrate and including a coordinator compound having an oxygen-reducing catalytic function; and
an enzyme-fixed layer covering said oxygen electrode layer.

3. The enzyme sensor according to claim 2, wherein said coordinator compound consists of a cyclic nitrogen-containing compound.

4. The enzyme sensor according to claim 3, wherein said coordinator compound is at least one member selected from the group consisting of a porphyrin derivative, a phthalocyanine derivative and a phenanthroline derivative.

* * * * *

UNITED STATES PATENT AND TRADEMARK OFFICE
CERTIFICATE OF CORRECTION

PATENT NO. : 5,205,920
DATED : April 27, 1993
INVENTOR(S) : Noboru OYAMA et al It is certified that error appears in the above-identified patent and that said Letters Patent is hereby corrected as shown below:

Column 7, line 58, delete "glutaladehyde" and insert
    -- glutaraldehyde --.

In Column 9, line 45, delete "substance" and insert -- substrate --.

Signed and Sealed this

Seventh Day of December, 1993

*Attest:*

BRUCE LEHMAN

*Attesting Officer*     Commissioner of Patents and Trademarks